United States Patent [19]
Yamashita et al.

[11] Patent Number: 5,330,909
[45] Date of Patent: Jul. 19, 1994

[54] MONOCLONAL ANTIBODY SPECIFICALLY RECOGNIZING N-TERMINAL PORTION OF HUMAN CALCITONIN

[75] Inventors: Nobuhiko Yamashita, Takatsuki; Manabu Nakamoto, Nara; Ryoichi Okura, Nishinomiya; Isao Matsushita, Ikoma, all of Japan

[73] Assignee: Osaka Gas Company Limited, Osaka, Japan

[21] Appl. No.: 958,083

[22] Filed: Oct. 8, 1992

[30] Foreign Application Priority Data

Oct. 11, 1991 [JP] Japan ................... 3-263587

[51] Int. Cl.$^5$ ............... C07K 15/28; C12N 5/20; C12P 21/08
[52] U.S. Cl. ............... 435/240.27; 435/70.21; 530/388.24
[58] Field of Search ............... 436/548, 817; 435/7.94, 435/70.21, 240.27; 530/328, 388.24, 388.85, 307, 387.9

[56] References Cited

U.S. PATENT DOCUMENTS 4,499,080  2/1985  Duflot et al. .................. 530/328
4,689,220  8/1987  Sturmer et al. ................. 424/85.8

OTHER PUBLICATIONS

Seth et al., 1988, A sensitive and specific two-site enzyme-immunoassay for human calcitonin using monoclonal antibodies J. Endocrinol 119:351-357.

Hellstrom et al., 1985, In *Monoclonal Antibodies for Cancer Detection and Therapy* (Baldwin et al., eds), p. 20 Academic Press, London.

Motte, P., et al., The Journal of Immunology, vol. 138, 3332-3338, No. 10, May 15, 1987.

Motte, P., et al., Henry Ford Hosp. Med. J., vol. 35, Nos. 2 & 3, 129-132 (1987).

Racchetti, G., et al., Molecular Immunology, vol. 24, No. 11, pp. 1169-1176, 1987.

Scopsi, L., et al., Histochemistry 88:113-125 (1988).

*Primary Examiner*—David Saunders
*Assistant Examiner*—James L. Grun

[57] ABSTRACT

A monoclonal antibody specifically recognizing N-terminal portion of human calcitonin (hCT), a hybridoma producing said monoclonal antibody, a process for preparing said monoclonal antibody, and a method for detecting hCT which comprises the use of said monoclonal antibody are provided.

The above monoclonal antibody permits detection of hCT with high sensitivity.

4 Claims, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

| Cys | Gly | Asn | Leu | Ser | Thr | Cys | Met | Leu | Gly | Thr | Tyr | Thr | Gln | Asp | Phe |
|---|---|---|---|---|---|---|---|---|---|---|---|---|---|---|---|
| 1 | | | | 5 | | | | | 10 | | | | | 15 | |

```
          Asn Lys Phe His Thr Phe Pro Gln Thr Ala Ile Gly Val Gly Ala Pro
                   20                  25                  30
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
          Cys Gly Asn Leu Ser Thr Cys Met Leu Gly
          1               5                   10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
          Thr Tyr Thr Gln Asp Phe Asn Lys Phe His
          1               5                   10
```

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
          Thr Phe Pro Gln Thr Ala Ile Gly Val Gly Ala Pro
          1               5                   10
```

( 2 ) INFORMATION FOR SEQ ID NO:5:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
          Cys Gly Asn Leu Ser Thr Cys Met Leu Gly Thr Tyr Thr Gln Asp Phe
          1               5                   10                  15

Asn Lys Phe His Thr Phe
                        20
```

( 2 ) INFORMATION FOR SEQ ID NO:6:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
          Thr Tyr Thr Gln Asp Phe Asn Lys Phe His Thr Phe Pro Gln Thr Ala
          1               5                   10                  15
```

```
Ile Gly Val Gly Ala Pro
         20
```

1

MONOCLONAL ANTIBODY SPECIFICALLY RECOGNIZING N-TERMINAL PORTION OF HUMAN CALCITONIN

FIELD OF THE INVENTION

The present invention relates to a monoclonal antibody specifically recognizing N-terminal portion of human calcitonin (hCT), a hybridoma producing said monoclonal antibody, a process for preparing said monoclonal antibody, and a method for detecting hCT which comprises the use of said monoclonal antibody.

PRIOR ART

Calcitonin (CT) is a peptide hormone constituted of 32 amino acids and is secreted from thyroid gland C-cells in mammals. As a major physiological action of this hormone, there is known its action to decreasing calcium level in blood by stimulating absorption in bone, its action of decreasing phosphorus level in blood by accelerating excretion of inorganic phosphorus into urine in the kidney, and the like.

Determination of calcitonin can be carried out by a biological method using as an indicator its action to decrease calcium level in serum in a rat, but this method is less sensitive and has not been used for the determination of calcitonin level in blood. In 1969, Clark et al. established a new method for determining calcitonin level by radioimmunoassay (RIA) using, as an antigen, calcitonin extracted from thyroid medullary carcinoma tissue. Subsequently, an RIA method utilizing synthetic human calcitonin has been developed, and the method has been widely utilized for detecting human calcitonin in blood. The determination of calcitonin in blood is clinically useful for diagnosis of thyroid medullary carcinoma, observation therapeutical progress, screening of familial thyroid medullary carcinoma, and diagnosis of ectopic CT-producing tumor. Furthermore, it is essential in a clinical study of calcium metabolism, as parathyroid hormone (PTH) is.

A RIA kit presently marketed for determining human calcitonin in blood utilizes an anti-human calcitonin polyclonal serum. However, such antiserum is unique to the particular animal used for immunization and it is difficult to obtain an antiserum having uniform quality. Accordingly, the antiserum has the defect that it is not possible to assemble a clinical kit having stable quality. Furthermore, the antiserum is a mixture of antibodies against various epitopes, and therefore, decomposition products other than monomer calcitonin also may be detected when calcitonin in serum is determined using the polyclonal antiserum. Thus, it is not possible to accurately determine concentration of calcitonin by the RIA method utilizing the polyclonal antiserum.

A monoclonal antibody specifically bound to human calcitonin recognizes only a particular portion (epitope) of human calcitonin and binds thereto. Accordingly, it is believed that construction of a measuring system by a sandwich technique, which utilizes two monoclonal antibodies recognizing different epitopes of human calcitonin, enables the specific determination of monomer calcitonin without interference from decomposition products, etc. Presently, there exist several reports on production of a monoclonal antibody against human calcitonin, and monoclonal antibodies have been obtained which recognize central portion or C-terminal portion of human calcitonin [L. Scopsi et al., "Monoclonal Antibodies against Calcitonin", *Histochemistry* 88, 113–125 (1988); Philippe Motte et al., "A Two-Site Immunoradiometric Assay for Serum Calcitonin using Monoclonal Anti-Peptide Antibodies", *Henry Ford Hosp. Med. J.* 35, 129–132 (1987)]. However, there is no example wherein a monoclonal antibody which can recognize N-terminal portion of calcitonin is produced.

BRIEF DESCRIPTION OF THE INVENTION

Thus, the present invention provides a monoclonal antibody specifically recognizing N-terminal portion of human calcitonin (hCT).

The present invention further provides a hybridoma producing said monoclonal antibody, a process for preparing said monoclonal antibody, and a method for detecting hCT which comprises using said monoclonal antibody.

DETAILED DESCRIPTION OF THE INVENTION

Figure 1:
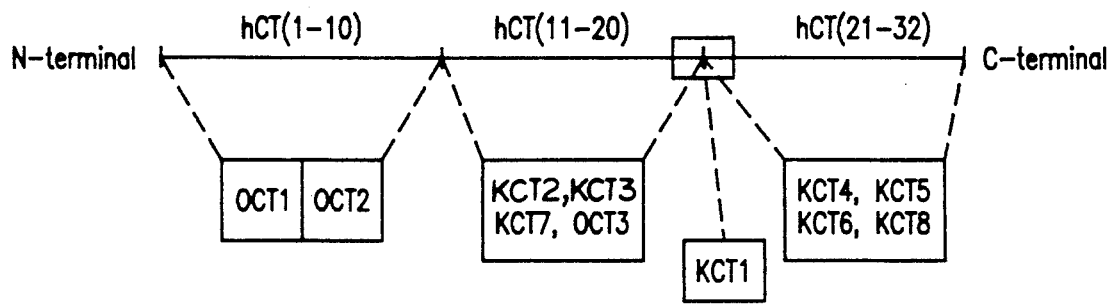
FIG. 1 shows the correspondence of epitopes of human calcitonin and monoclonal antibodies specific to them.

When a monoclonal antibody against a low molecular weight antigen such as a hormone is prepared, immunization is generally carried out after binding the low molecular weight antigen to a higher molecular weight molecule such as a protein so that an immune system of a living body can easily recognize the target antigen in the process for preparing said antibody. As an agent for cross-linking the low molecular weight antigen to the higher molecular weight molecule such as a protein, glutaraldehyde or a water-soluble carbodiimide is usually employed.

The present inventors have made an intensive investigation to obtain a monoclonal antibody specifically recognizing N-terminal portion of human calcitonin, and have succeeded in obtaining such antibody by a method which comprises using 1-ethyl-3-(3-dimethylaminopropyl)-carbodiimide (EDC) as a cross-linking agent to bind human calcitonin to ovalbumin in the process for preparing said monoclonal antibody using human calcitonin as an antigen, and immunizing an animal with the resultant conjugate as an antigen.

Thus, the present monoclonal antibody specifically recognizing N-terminal portion of human calcitonin can be prepared as follows:

a) using 1-ethyl-3-(3-dimethylaminopropyl)-carbodiimide as a cross-linking agent to bind human calcitonin to ovalbumin, and immunizing a mouse with the resultant conjugate as an antigen;

b) fusing spleen cells from said mouse with myeloma cells of a mouse, and selecting a hybridoma producing a monoclonal antibody specifically recognizing N-terminal portion of human calcitonin; and c) cultivating said hybridoma under suitable conditions, and recovering said monoclonal antibody.

The peptide-protein conjugate of the above step a) can be prepared by mixing and reacting the peptide, protein and cross-linking agent in water or in a suitable buffered solution. After the reaction is completed, the reaction mixture is dialyzed against a suitable solvent, and the dialyzed solution is used as an antigen solution.

In addition, the immunization of a mouse in step a) may be carried out by mixing the above antigen solution with a suitable adjuvant to prepare an adjuvant solution and administering the latter solution to the mouse. Booster immunization with the same antigen may be carried out after an appropriate lapse of time. A preferred mouse to be immunized is a Balb/c mouse.

The cell fusion of the above step b) can be carried out by a conventional method. The myeloma cells of a mouse include cell lines such as SP2/0-Ag14 and P3-NSI-1-Ag4-1. The cell fusion may be carried out using, for example, polyethylene glycol or electroporation procedures.

Furthermore, the selection of the resultant hybridomas in the step b) can be carried out, for example, by enzyme-linked immunosorbent assay (ELISA). Thus, various fragments of human calcitonin are allowed to react with the cultured medium obtained by cultivating the hybridomas in a suitable medium, and the hybridomas producing antibody which reacts only with a fragment containing N-terminal portion of human calcitonin are selected. Subsequently, the selected hybridomas are cloned by the limiting dilution method.

The recovery of the monoclonal antibody in the step c) can be carried out by a conventional method, for example, by implanting the hybridoma clone obtained in the step b) into the peritoneal cavity of a mouse and then recovering the antibody from the ascites fluid of the mouse. Alternatively, the monoclonal antibody may be recovered from a cultured medium of the hybridoma clone cultivated using a large-scale culture apparatus. Furthermore, the antibody recovered may be purified by a conventional purification method, such as ammonium sulfate precipitation, molecular sieve chromatography, affinity chromatography, or the like.

The monoclonal antibodies of the present invention can be used for determining human calcitonin in serums. Assays for such determination include radioimmunoassay (RIA), enzyme immunoassay (EIA), fluoroimmunoassay (FIA), or the like. The present antibodies may be used according to the procedures usually used in these assays.

Furthermore, when labelling of antibody is required, it may be carried out according to a conventional method using a label well known in the art such as an enzyme, fluorescent substance or radioisotope.

The present invention is further illustrated by the following Examples, but should not be construed to be limited thereto.

EXAMPLE 1

Preparation of Anti-Human Calcitonin Monoclonal Antibodies

A. Chemical Synthesis and Purification of Calcitonin Analogues

Calcitonin analogue peptides were chemically synthesized using an automated peptide synthesizer (ABI MODEL 430A, Applied Biosystems). The peptides synthesized are shown in Table 1. All of hCT(1-10), hCT(11-20), hCT(21-32), hCT(1-22) and hCT(11-32) are peptide fragments derived from human calcitonin. Both of hCT(21-32) and hCT(11-32) were synthesized in such a manner that C-terminals of them would have an amide structure.

TABLE 1

| | Synthesized hCT fragments | |
|---|---|---|
| | N-terminal | C-terminal |
| hCT(1-32): | CGNLSTCMLGTYTQDFNKHTFPQTAIGVGAP-NH₂ CGNLSTCMLGTYTQDFNKHTFPQTAIGVGAP is identified in the Sequence Listing as SEQ ID NO: 1 | |
| hCT(1-10): | CGNLSTCMLG which is identified in the Sequence Listing as SEQ ID NO: 2 | |
| hCT(11-20): | TYTQDFNKH which is identified in the Sequence Listing as SEQ ID NO: 3 | |
| hCT(21-32): | TFPQTAIGVGAP-NH₂ wherein TFPQTAIGVGAP is identified in the Sequence Listing as SEQ ID NO: 4 | |
| hCT(1-22): | CGNLSTCMLGTYTQDFNKHTF which is identified in the Sequence Listing as SEQ ID NO: 5 | |
| hCT(11-32): | TYTQDFNKHTFPQTAIGVGAP-NH₂ wherein TYTQDFNKFHTFPQTAIGVGAP is identified in the Sequence Listing as SEQ ID NO: 6 | |

Both of hCT(21-32) and hCT(11-32) which have amide structure at their C-terminals were synthesized by the t-butyloxycarbonyl (t-Boc) method using p-methylbenzhydrylamine (BHA) resin as a solid phase. Cleavage from the resin and deprotection of the products following the synthesis was carried out using trifluoromethanesulfonic acid (TFMSA). The other peptides were synthesized by the 9-fluorenylmethyloxycarbonyl (Fmoc) method using p-hydroxymethylphenoxymethylpolystyrene (PIMP) resin as a solid phase. Cleavage from the resin and deprotection of the products following the synthesis was carried out using trifluoroacetic acid (TFA).

The synthesized peptides which had been cleaved from the resins were purified by high-performance reverse phase chromatography using Waters μBONDASPHERE 5μ C18-300Å (3.9 mm×15 cm) column. Amino acid sequences of the purified peptides were analyzed by using a Protein Sequencer MODEL 477A (Applied Biosystems).

B. Preparation of Antigens

In order to enhance antigenicity, the human calcitonin peptides were bound to two carrier proteins using two cross-linking agents. Thus, ovalbumin and key hole limpet hemocyanin (KLH) were used as the carrier proteins, and 1-ethyl-3-(3-dimethylaminopropyl)carbodiimide (EDC) and glutaraldehyde were used as the cross-linking agents.

To 25 mg/ml of aqueous human calcitonin solution (22.4 μl) were added 10 mg/ml of aqueous ovalbumin solution (16.8 μl) and 100 mg/ml of EDC (16.8 μl), and the mixture was reacted overnight in the dark at room temperature. Water was then added to the mixture to obtain 1 ml of total volume and the mixture was dialyzed against distilled water and used as a hCT-ovalbumin antigen solution. On the other hand, 0.1M sodium phosphate solution, pH 7.0 (100 μl), containing 20% glutaraldehyde was added to 0.1M sodium phosphate solution, pH 7.0 (200 μl), containing 1.87 mg/ml of human calcitonin and 3.1 mg/ml of KLH, and the mixture was reacted at room temperature for 1 hour with stirring. Subsequently, 0.1M sodium phosphate solution, pH 7.0 (200 μl), containing 1M glycine was added to the mixture, and the resultant mixture was stirred at room temperature for a further 1 hour. The reaction mixture was dialyzed against 0.1M sodium phosphate solution, pH 7.0, and used as a hCT-KLH antigen solution. The two antigen solutions were stored at 4° C. until use.

C. Immunization of Mice

Immunization of mice with a human calcitonin-carrier protein antigen was carried out using as an adjuvant Ribi Adjuvant System (KIBI IMMUNOCHEM RESEARCH INC.). Thus, the adjuvant and each of the antigen solutions were mixed at a ratio of 1:1 to prepare two adjuvant solutions respectively containing 20 μg/ml and 200 μg/ml of human calcitonin. Each of the adjuvant solutions (0.2 ml aliquots) was administered to peritoneal cavity of four Balb/c mice (male; 8 weeks old) every two weeks, five times in total. Every three days after the administration, blood samples were taken from tails of the immunized mice, and antibody activity to human calcitonin in sera and subclasses of the antibodies were monitored. The subclass of the antibodies in serum having a binding activity to hCT was determined by the ELISA method using a Mouse Typer Sub-Isotyping Kit (Bio-Rad Laboratories). Mice, which had an elevated antibody activity, said antibody belonging to IgG subclass, were selected and used as donors of spleen cells utilized for cell fusion with myeloma cells.

D. Cell Fusion

To the spleen cells-donating mice selected in the above step C was intravenously administered 4 μg or 40 μg of hCT-ovalbumin or hCT-KLH, and three days after the administration the spleen was removed from each mouse. The spleen cells and myeloma cells (PAI) [T. Arai et al., *Monoclonal Antibodies*, Japan Biochemistry Society ed., Seikagaku-Jikken Koza No.6, "Structure and Function of Cell Skeleton", pp.489–503, Tokyo Kagaku Dojin, Tokyo, 1989]were mixed at a ratio of 5–10:1, and 75 mM Hepes [Boehringer Mannhelm GmbH, W., Germany](1 ml) containing 50% (w/v) polyethylene glycol 1500 was added to the mixture to allow cell fusion. The fused hybridomas were selected in HAT medium.

E. Selection and Cloning of Hybridomas Producing Anti-Human Calcitonin Antibody Hybridomas producing anti-human calcitonin antibody were screened by the ELISA method using human calcitonin as an antigen. A 50 mM sodium bicarbonate solution, pH 9.6 (50 μl), containing 1 μg/ml of human calcitonin peptide was charged onto 96-well microtiter plates [COSTAR, CAT. No. 3590]and allowed to stand at 4° C. for 12 hours. As a control, a similar procedure was repeated using a control solution (50 μl) free of the antigen. After removing the antigen solution and control solution from each of the wells, the surface of the wells was blocked by treating it with 25% Block Ace [Yukijirushi Nyugyo Co.; a powdery agent mainly containing 1% milk protein and an organic acid buffer, which is used for blocking the surface of wells of ELISA plates.]solution (200 μl) at room temperature for 1 hour. The blocking solution was then removed, and each of the wells was washed three times with PBS containing 0.05% (v/v) Tween 20 (PBS-Tween) (200 μl). After removing the washing solution, a sample solution (50 μl) containing a first antibody was charged into each of the wells and the mixture was allowed to stand at room temperature for 2 hours to effectuate antigen-antibody reaction. Then, the sample solution was removed and the plate was washed again four times with PBS-Tween. In order to detect the first antibody bound to the antigen on the plate, PBS-Tween (50 μl) containing a 3000-fold diluted, horseradish peroxidase-labelled secondary antibody [Bio-Rad Laboratories-]against the primary antibody was charged into each of the wells and antigen-antibody reaction was allowed to take place. After allowing the mixture to stand at room temperature for 2 hours, the enzyme-labelled secondary antibody solution was removed and each of the wells was washed four times with PBS-Tween (200 μl). In order to detect the secondary antibody bound to the primary antibody, 100 mM sodium citrate solution, pH 4.5 (200 μl), containing 0.4% (w/v) of o-phenylenediamine and 0.014% (v/v) of 30% aqueous hydrogen peroxide was charged into each of the wells to obtain coloring reaction. After 15 minutes, 6N sulfuric acid (50 μl) was added to terminate the reaction and absorbance at 490 nm was measured using a Micro Plate Reader [Model 3550; Bio-Rad Laboratories]. The difference between the absorbance in each of the wells in which the antigen was adsorbed and that in the control was assessed as the binding activity of the sample antibody to the antigen.

In ELISA, a peptide antigen is directly bound to a plate, and therefore, the antigen may be structurally denatured as compared with that in free state in solution. Accordingly, in order to study the binding property of the antibody to a free antigen, an absorption experiment was performed. Thus, various concentrations of a competitive peptide were added to a sample antibody solution and allowed to react overnight at 4° C. After the reaction, ELISA was performed using an ELISA plate previously coated with human calcitonin (50 ng).

Hybridomas in the wells, wherein an anti-human calcitonin antibody was detected in the supernatant, were cloned by the limiting dilution method. The cloning was performed two times per hybridoma in one well. The hybridomas were cultivated in DMEM medium containing 15% fetal bovine serum.

F. Preparation and Purification of Monoclonal Antibody from Ascites Fluid of Mouse In order to diminish immune activity in a mouse body to facilitate production of ascites fluid, 2,6,10,14-tetramethylsentadecane (1 ml) was intraperitoneally administered to a Balb/c mouse (male; 8 weeks old). About ten days after the administration, DMEM solution (0.5 ml) containing $10^7$ of cells hybridomas was injected intraperitoneally into the mouse. About two weeks after the injection, ascites fluid was recovered from the mouse and cells in the fluid were removed by centrifugation at 1000 xg. From the resultant supernatant, a monoclonal antibody was obtained and purified by affinity chromatography using a Protein A column [Bio-Rad Laboratories Co. Ltd].

G. Characteristics of Anti-Human Calcitonin Monoclonal Antibody

As a result of cell fusion which was performed using spleen cells obtained from one mouse immunized with 40 μg of hCT-KLH antigen and one mouse immunized with 40 μg of hCT-ovalbumin antigen, 11 strains of hybridomas producing anti-human calcitonin monoclonal antibody were cloned. Among them, eight hybridoma clones derived using hCT-KLH antigen were designated as hybridomas KCT1 to KCT8, and three hybridoma clones derived using hCT-ovalbumin antigen were designated as hybridomas OCT1 to OCT3. Furthermore, monoclonal antibodies produced by these hybridomas were designated as MAbs KCT1 to KCT8 and MAbs OCT1 to OCT3, respectively.

Determination of subclasses of the antibodies obtained from ascites fluid revealed that only one monoclonal antibody MAb OCT3 belongs to isotype $IgG_{2b}$ and the other monoclonal antibodies belong to isotype $IgG_1$.

Epitopes of the resultant monoclonal antibodies were determined by the ELISA method using various fragments of human calcitonin (Table 2 and Table 3).

TABLE 2

Reactivity of monoclonal antibodies to synthesized hCT fragments (ELISA)

| | Monoclonal antibodies (MAbs) | | | | | | | | | | |
|---|---|---|---|---|---|---|---|---|---|---|---|
| | KCT1 | KCT2 | KCT3 | KCT4 | KCT5 | KCT6 | KCT7 | KCT8 | OCT1 | OCT2 | OCT3 |
| hCT(1-32): | + | + | + | + | + | + | + | + | + | + | + |
| hCT(1-10): | − | − | − | − | − | − | − | − | + | ± | − |
| hCT(11-20): | − | + | + | − | − | − | + | − | − | − | + |
| hCT(21-32): | − | − | − | + | + | + | − | + | − | − | − |
| hCT(1-22): | ± | + | + | − | − | − | + | − | + | + | + |
| hCT(11-32): | ± | − | + | + | + | + | + | + | − | − | + |

TABLE 3

Reactivity of monoclonal antibodies to synthesized hCT fragments (Absorption experiment)

| | Monoclonal antibodies (MAbs) | | | | | | | | | | |
|---|---|---|---|---|---|---|---|---|---|---|---|
| | KCT1 | KCT2 | KCT3 | KCT4 | KCT5 | KCT6 | KCT7 | KCT8 | OCT1 | OCT2 | OCT3 |
| hCT(1-32): | ± | + | + | + | + | ± | + | + | ± | + | + |
| hCT(1-10): | − | − | − | − | − | − | − | − | + | + | − |
| hCT(11-20): | − | ± | + | − | − | ± | − | − | − | − | + |
| hCT(21-32): | − | − | − | + | + | ± | − | + | − | − | − |
| hCT(1-22): | − | + | + | − | − | − | + | − | ± | + | + |
| hCT(11-32): | − | + | + | − | − | ± | − | + | − | − | + |

As a result, it was found that monoclonal antibodies mainly recognizing central portion or C-terminal portion of human calcitonin were derived from a mouse immunized with a conjugate prepared by binding human calcitonin via glutaraldehyde to KLH, as an antigen (MAbs KCT1 to KCT8). On the other hand, monoclonal antibodies mainly recognizing N-terminal portion of human calcitonin were derived from a mouse immunized with a conjugate prepared by binding human calcitonin via EDC to ovalbumin, as an antigen (MAbs OCT1 and OCT2). It is believed that this difference is attributed to the difference in structures of peptide-carrier proteins due to the difference in cross-linking agents used.

Furthermore, it was found that the antibodies recognizing N-terminal portion could be divided into two subgroups. MAb OCT1 binds to peptides containing N-terminal portion of amino acid sequence of human calcitonin, hCT(1-10) and hCT (1-22), and therefore, it is believed that its epitope exists within 10 residues of the N-terminal portion of the amino acid sequence. On the other hand, MAb OCT2 does not bind to hCT(1-10), but binds to hCT(1-22). However, absorption experiment reveal that binding activity of MAb OCT2 to human calcitonin is absorbed by hCT(1-10). This fact demonstrates that the antibody can bind to free hCT(1-10), but cannot bind to hCT(1-10) bound to an ELISA plate. Thus, it was found that MAb OCT2 clearly differs from MAb OCT1 in its properties. In addition, MAb KCT1 binds only to hCT(1-32) and hCT (11-32), and does not bind to hCT(1-10), hCT (11-20) and hCT (21-32). Accordingly, it is believed that its epitope exists around a boundary site of hCT(11-20) and hCT(21-32).

The above results are summarized in Table 4 and FIG. 1.

TABLE 4

Results of purification of anti-hCT monoclonal antibodies

| No. | Clone | Isotype | Epitope | Purified amount (mg) |
|---|---|---|---|---|
| 1 | KCT1 | IgG1, κ | hCT(11-20)-hCT(21-32) | 8.7 |
| 2 | KCT2 | IgG1, κ | hCT(11-20) | 21.8 |
| 3 | KCT3 | IgG1, κ | hCT(11-20) | 1.8 |
| 4 | KCT4 | IgG1, κ | hCT(21-32) | 20.3 |
| 5 | KCT5 | IgG1, κ | hCT(21-32) | 9.6 |
| 6 | KCT6 | IgG1, κ | hCT(21-32) | 13.6 |
| 7 | KCT7 | IgG1, κ | hCT(11-20) | 12.1 |
| 8 | KCT8 | IgG1, κ | hCT(21-32) | 25.2 |
| 9 | OCT1 | IgG1, κ | hCT(1-10) | 30.2 |
| 10 | OCT2 | IgG1, κ | hCT(1-10) | 30.8 |
| 11 | OCT3 | IgG2b, κ | hCT(11-20) | 20.5 |

The above hybridomas OCT1 and OCT2 (producing MAbs OCT1 and OCT2, respectively) according to the present invention were deposited at the Fermentation Research Institute Agency of Industrial Science and Technology, 1-3, Higashi 1 chome Tsukuba-shi Ibaraki-ken 305, JAPAN, under the accession numbers of FERMs P-12532 and P-12533, respectively (Date of Deposit: Sep. 26, 1991). The depositions were then changed to international depositions under the Budapest Treaty and assigned the new deposition numbers FERMs BP-4001 and BP-4002 (Date of Transfer: Sep. 9, 1992).

EXAMPLE 2

Construction of Sandwich Assay System Using Monoclonal Antibodies

A sandwich assay system was constructed using MAbs KCT2 and OCT2, and its detection sensitivity was examined. MAb OCT2 was labelled with biotin using a Biotinilation Kit (Amersham International plc). Each of the wells of an ELISA plate was coated with 10 μg/ml of MAb KCT2 (primary antibody) (50 μl) and maintained at 4° C. overnight. To each of the wells was then added 10% Block Ace solution containing various concentrations of human calcitonin or serum [SCANTIBODIES LABORATORY, INC.]not containing calcitonin (50 μl), and the plate was kept at 15° C. for 5 hours to allow reaction. Subsequently, 0.3 μg/ml of biotin-labelled MAb OCT2 (secondary antibody) was added to each of the wells, and kept at 4° C. for 15 hours for reaction. In order to detect the secondary antibody, coloring reaction was performed using Vecstain Elite ABC Kit [Vector Laboratories, Inc.]and 3,3', 5,5'-tetramethylbenzidine (TMB) Microwell Peroxidase Substrate System [Kirkegaard & Perry Laboratories Inc.]. After the termination of the enzyme reaction, absorbance was determined at 450 nm.

Figure 2:
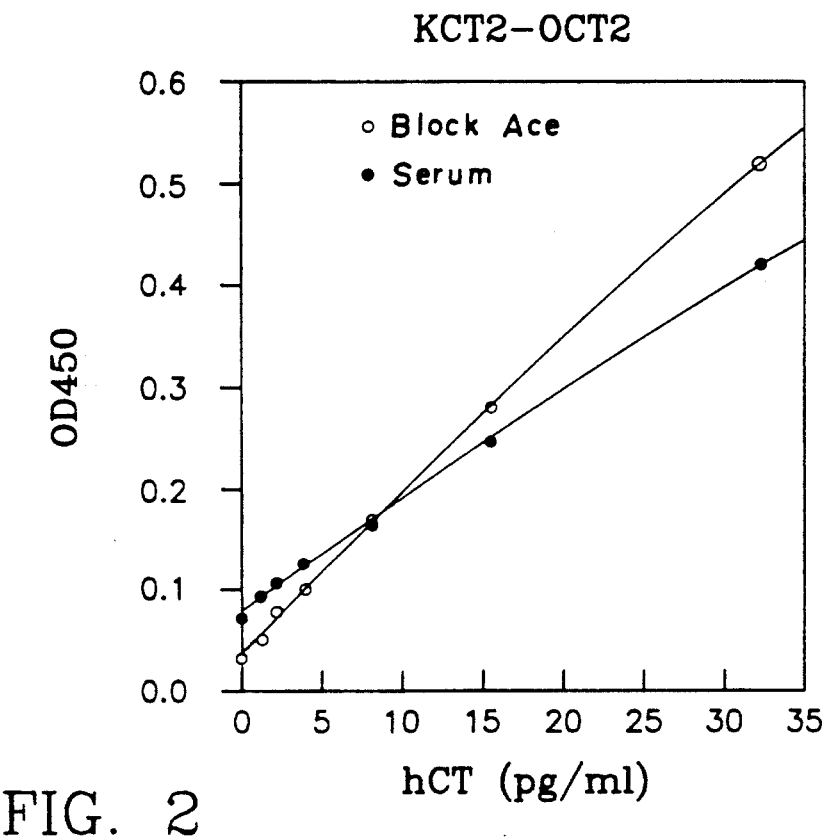
FIG. 2 shows the results of determining human calcitonin by a sandwich technique using MAb KCT2 - MAb OCT2.

As a result, it was found that the sandwich assay utilizing the combination of MAb KCT2 and MAb OCT2 can detect about 4 pg/ml concentration of human calcitonin in serum (FIG. 2).

EXAMPLE 3

Analysis of Serum From Patient Having Thyroid Medullary Carcinoma

It has been known that the concentration of human calcitonin is very high in serum from a patient having thyroid medullary carcinoma. In order to confirm this, analysis of human calcitonin in serum was conducted. Thus, serum from the patient was fractionated by high performance molecular sieve chromatography, and the fractionated serum was analyzed by a sandwich assay utilizing combinations of various antibodies and by a commercially available kit. Human serum was fractionated by high performance molecular sieve chromatography utilizing Shodex PROTEIN KW-803 column (8 mm×30 cm; a set of two columns). As a pumping system there was used a Waters 600E Multisolvent Delivery System. The column was previously equilibrated with 0.1M potassium phosphate buffer, pH 7.0, containing 0.2M NaCl. A serum sample (100 μl) was charged onto the column and developed at flow rate of 1.0 ml/minute. Absorbance at 280 nm was monitored with a Waters 484 Tunable Absorbance Detector and the results were recorded using a Waters 741 Data Module. Eluate was fractionated into several portions, each 0.5 ml, and a 50 μl aliquot was used for ELISA and a 10 μl aliquot for RIA.

The RIA kit used was purchased from Bacster Co. In certain experiments, human calcitonin antiserum (Dako Japan Co.) was used as a secondary antibody. Protein markers for determination of molecular weight in HPLC were purchased from Oriental Yeast Industries Co. Glutamate dehydrogenase (Mw 290,000), lactate dehydrogenase (Mw 142,000), enolase (Mw 67,000), adenylate kinase (Mw 32,000), and cytochrome c (Mw 12,400) were used as molecular weight markers.

Figure 3:
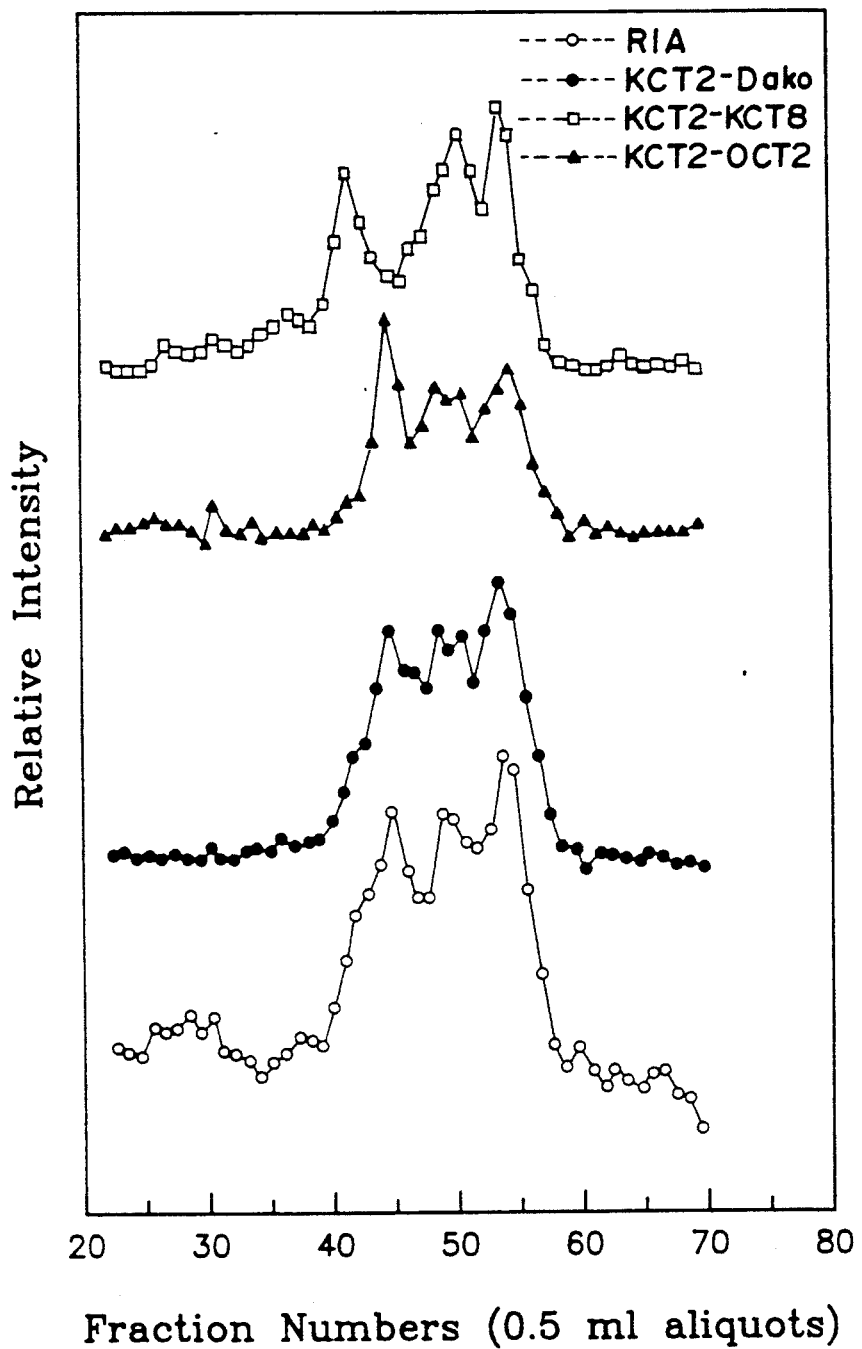
FIG. 3 shows the results of examining serum from a patient having thyroid medullary carcinoma by a sandwich technique using various combinations of monoclonal antibodies.

The fractions obtained by subjecting serum of the patient to high performance molecular sieve chromatography were analyzed with the RIA kit, and five peaks were observed including non-separated peaks in a larger molecular weight region in addition to a peak of monomer human calcitonin (FIG. 3). These peaks were believed to be those of a polymer of human calcitonin or those of a conjugate of calcitonin and other protein, because they disappeared by reducing the fractions (data not shown). On the other hand, on analyzing the same fractions by a sandwich assay utilizing MAb KCT2 - MAb KCT8, a peak of human calcitonin as well as four peaks in the larger molecular weight region were similarly detected. In comparison with the results of the analysis using the RIA kit, it was found that the analysis by the sandwich assay utilizing MAb KCT2 - MAb KCT8 did not detect one of the peaks detected by RIA in the larger molecular weight region. Next, a similar analysis was carried out by a sandwich assay in which the secondary antibody was changed to MAb OCT2 recognizing N-terminal of calcitonin (MAb KCT2 - MAb OCT2). As a result, it was found that this assay did not detect the peak which was detected in the region of the largest molecular weight in the RIA and MAb KCT2 - MAb KCT8 assays. On the contrary, when a sandwich assay was conducted using a commercially available polyclonad antibody as a secondary antibody, the type and pattern of the detected peaks were approximately similar to those of RIA. These results suggest that it would be possible to construct a sandwich assay system which can detect only monomer human calcitonin by properly selecting monoclonal antibodies.

What is claimed is:

1. A monoclonal antibody MAb OCT1 which is produced by hybridoma OCT1 having accession number FERM BP-4001 and specifically recognizes N-terminal portion of human calcitonin.

2. A monoclonal antibody MAb OCT2 which is produced by hybridoma OCT2 having accession number FERM BP-4002 and specifically recognizes N-terminal portion of human calcitonin.

3. A hybridoma OCT1 having accession number FERM BP-4001.

4. A hybridoma OCT2 having accession number FERM BP-4002.

* * * * *